United States Patent [19]

Myers et al.

[11] Patent Number: 4,496,779
[45] Date of Patent: Jan. 29, 1985

[54] PROCESS FOR THE HYDROXYLATION OF OLEFINS USING MOLECULAR OXYGEN, AN OSMIUM CONTAINING CATALYST, A COPPER CO-CATALYST, AND A CYCLOALIPHATIC AMINE BASED PROMOTER

[75] Inventors: Richard S. Myers, Fairlawn; Robert C. Michaelson, Kinnelon; Richard G. Austin, Ridgewood, all of N.J.

[73] Assignee: Exxon Research & Engineering Co., Florham Park, N.J.

[21] Appl. No.: 604,043

[22] Filed: Apr. 26, 1984

[51] Int. Cl.³ .................... C07C 29/04; C07C 31/18; C07C 31/22; C07C 31/42
[52] U.S. Cl. .................... 568/860; 260/397.2; 560/186; 562/587; 568/811; 568/821; 568/833; 568/838; 568/847
[58] Field of Search ............... 568/860, 833, 811, 821, 568/838, 847; 562/587; 560/186; 260/397.2

[56] References Cited

U.S. PATENT DOCUMENTS

| | | | |
|---|---|---|---|
| 2,773,101 | 12/1956 | Smith et al. | 568/860 |
| 3,317,592 | 5/1967 | Maclean et al. | 568/860 |
| 3,337,635 | 8/1967 | Norton et al. | 568/860 |
| 4,390,739 | 6/1983 | Michaelson et al. | 568/860 |

FOREIGN PATENT DOCUMENTS 32522 8/1974 Japan ................................ 568/860

*Primary Examiner*—J. E. Evans
*Attorney, Agent, or Firm*—Robert A. Maggio

[57] ABSTRACT

A process directed to the hydroxylation of olefins by reacting said olefins in the presence of oxygen, water, and a catalyst composition comprising (i) a catalytically active osmium containing compound, (ii) a Co-catalyst I comprising a copper containing compound such as $CuBr_2$, and (iii) a Co-catalyst II capable of increasing the rate and/or selectivity of the hydroxylation reaction, such as 1,4-diazabicyclo [2.2.2.] octane is disclosed.

28 Claims, No Drawings

PROCESS FOR THE HYDROXYLATION OF OLEFINS USING MOLECULAR OXYGEN, AN OSMIUM CONTAINING CATALYST, A COPPER CO-CATALYST, AND A CYCLOALIPHATIC AMINE BASED PROMOTER

BACKGROUND OF THE INVENTION

The present invention relates to a process for converting olefinically unsaturated compounds directly to their corresponding diols or polyols in the presence of a specifically defined oxidation catalyst composition, water, and an oxygen containing gas.

It is well known from the technical literature, that olefins can be oxidized to their corresponding diols, stoichiometrically or catalytically with osmium oxide compounds, particularly osmium tetroxide.

The non-catalytic, i.e. stoichiometric, cis-hydroxylation of alkenes with $OsO_4$ has been conventionally characterized as taking place via the formation, with the alkene, of an osmium (VI) intermediate ester complex. [For a recent review, see, "Osmium Tetroxide Cis Hydroxylation of Unsaturated Substrates", by M. Schroder, Chem. Rev. Vol 80, pp. 187–213 (1980) hereinafter Schroder].

To convert the non-catalytically prepared osmium (VI) ester complex intermediate to the diol, the intermediate can be hydrolyzed reductively. Reductive hydrolysis is conventionally carried out by using alkali metal sulfites, bisulfites, lithium aluminum hydride, or hydrogen sulfide to yield the corresponding cis-diols together with lower valence forms of osmium which are removed by filtration.

It has been observed by Criegee (See Schroder, page 191, Col. 1 11–12) that for non-catalytic cis hydroxylation of alkenes, the rate of formation of the Osmium (VI) ester complex is greatly increased in the presence of tertiary amines such as pyridine. This rate enhancement is believed to occur via the formation of some type of amine Osmium (VI) ester complex (See Schroder page 191, Col. 2). However, enhancement of the rate of the Osmium (VI) ester complex does not necessarily result in an enhancement of the overall hydroxylation rate, since the rate of hydrolysis of the ester complex must also be considered. In this regard, it has been noted that whereas certain osmium ester complexes and amine ester complexes (e.g. with pyridine) can be hydrolyzed reductively, amine ester complexes are more resistant to such hydrolysis. (See Schroder page 191, Col. 2, last paragraph; and page 193, Col. 1, first paragraph).

In contrast to the stoichiometric non-catalytic mode of cis hydroxylation with $OsO_4$, the catalytic mode employs a secondary oxidant to oxidatively hydrolyze the intermediate Osmium (VI) ester and regenerate the $OsO_4$ which can undergo further reduction by the substrate olefin. A variety of oxidants have been employed in conjunction with $OsO_4$ such as $H_2O_2$, t-butylhydroperoxide and oxygen.

The use of oxygen as an oxidant has encountered considerable difficulty due to the appreciable overoxidation of the products, particularly at elevated temperatures (e.g. 70°–80° C.), leading to the formation of keto or acid products. However, if the reaction temperature is lowered to reduce overoxidation, the reaction rate is so low that yields of cis-diol are drastically reduced. An additional disadvantage of the use of oxygen oxidant is that the reaction is highly pH dependent (See Schroder, page 210, Col. 1).

The poor performance of oxygen based osmium catalyzed olefin hydroxylation systems is unfortunate, since such systems have inherent advantages over organic hydroperoxide based systems. For example, hydroxylation systems employing organohydroperoxide oxidants result in the conversion of the organohydroperoxide to its corresponding alcohol during the formation of the desired olefin derived diol. Thus, for example, t-butylhydroperoxide is converted to t-butylalcohol. The commercial attractiveness of such processes is dependent on the ability to use or sell the organic alcohol co-product in addition to the diol. Given the fluctuation in economic conditions, however, it may be difficult to dispose of large quantities of these organic alcohol co-products in an economically attractive manner. In any event, it can be troublesome, when the quantity of one product, selected on the basis of marketing possibilities for a given period, necessarily determines the quantity of some other product which may be smaller or larger than desirable in view of changing marketing requirements within that same period. It can, therefore, under certain circumstances be considered as a disadvantage of the aforenoted organohydroperoxide based processes that such large quantities of organic alcohols are formed as co-products, even though under other circumstances the formation of two products may well be found acceptable.

In contrast, oxygen based hydroxylation systems do not produce an oxidant derived alcohol co-product that must be disposed of, which can be a significant advantage.

The search has, therefore, continued for ways of improving the rate and/or selectivity of osmium catalyzed oxygen based processes for hydroxylating olefins.

One step in this direction, is disclosed in commonly assigned U.S. Pat. No. 4,390,739 by R. Austin and R. Michaelson. This patent describes a process for the hydroxylation of olefins using oxygen as an oxidant, a catalytically active metal oxide catalyst such as $OsO_4$, and at least one transition metal salt co-catalyst such as copper bromide. This process can also be conducted in the optional presence of a second co-catalyst such as alkali metal halides. Pyridine is disclosed as a suitable solvent for this process but no mention is made of any promoting effect being associated with this solvent medium. While the use of the transition metal co-catalyst substantially improves the reaction rate and/or selectivity of the hydroxylation reaction, a further improvement in this process is still being sought.

U.S. patent application Ser. No. 310,217, filed Oct. 9, 1981, now abandoned, of common assignee herein by R. Michaelson and R. Austin discloses the use of various osmium halide and oxyhalide catalysts in the presence or absence of a wide variety of co-catalysts and an oxidant selected from hydrogen peroxide, organohydroperoxides, or oxygen. Pyridine is disclosed as a suitable buffer for pH control in this application, which pH control is required when employing hydrogen peroxide.

Commonly assigned U.S. Pat. No. 4,314,088 and a continuation-in-part thereof, namely, U.S. Pat. No. 4,393,253 by R. Austin and R. Michaelson collectively, disclose the use of various halide containing co-catalysts in conjunction with osmium tetroxide catalyst and organohydroperoxide oxidants to hydroxylate olefins. The halide containing co-catalysts include alkali and alkaline earth metal halides, hydrogenhalides, quaternary hydrocarbyl phosphonium halides, halogens, and transition metal halides.

U.S. patent application Ser. No. 399,270 filed July 19, 1982, by R. Austin and R. Michaelson is directed to a process for hydroxylating olefins in the presence of an organohydroperoxide oxidant, an osmium containing catalyst and an organic halogenated hydrocarbon co-catalyst.

Commonly assigned U.S. patent application Ser. No. 394,414, filed July 1, 1982 by R. Michaelson and R. Austin, is directed to the use of carboxylate salts as co-catalysts for use in conjunction with osmium oxides as a catalyst and organohydroperoxide as oxidant to hydroxylate olefins.

Commonly assigned U.S. Pat. No. 4,413,151, by R. Michaelson, R. Austin, and D. White is directed to a process for hydroxylating olefins in the presence of a supported osmium containing catalyst, optional co-catalyst (e.g. $CuBr_2$) and an oxidant selected from hydrogen peroxide, organohydroperoxides and oxygen.

Commonly assigned U.S. patent application Ser. No. 420,137 filed Sept. 20, 1982 by R. Michaelson, R. Austin and D. White is directed to a process for hydroxylating olefins in the presence of an osmium carbonyl catalyst optional co-catalysts and an oxidant selected from hydrogen peroxide, organohydroperoxide, and oxygen.

Commonly assigned U.S. patent application Ser. No. 440,964, filed Nov. 12, 1982 by R. Michaelson, R. Austin, and D. White is directed to a process for hydroxylating olefins in the presence of an osmium oxide catalyst, optional co-catalysts and sodium hydroxide as a co-catalyst.

While all of the above described commonly assigned patents or patent applications disclose the use of pyridine as one of many suitable solvents, none of these applications show or suggest either alone or collectively, that any promoting effect can be obtained from pyridine when employed in accordance with the presently claimed invention.

Moreover, to the best of the inventors' knowledge, not a single prior art publication shows the use of any tertiary amine as a promoter to enhance the overall rate of osmium catalyzed cis-hydroxylation of olefins with oxygen. The catalytic cis hydroxylation of tetra and tri-substituted alkenes with t-butylhydroperoxide and $OsO_4$ has apparently been conducted. However, the oxidative hydrolysis of such esters has been found to be particularly slow due to steric considerations and particularly in the presence of pyridine (See, Schröder, page 193, Col. 2, first paragraph).

Commonly assigned U.S. patent application Ser. No. 538,190, filed Oct. 3, 1983 by the inventors herein is directed to the use of heteroaromatic and pseudoheteroaromatic amine promoters, such as pyridine, in a similar reaction system to that described herein.

Notwithstanding the above, the following discussion is intended to provide a background of osmium based olefin hydroxylation processes.

U.S. Pat. No. 3,335,174, is directed to the use of Group Vb, VI-b and VIII metal halides and oxyhalides (e.g., $OsCl_3$) as hydroxylation and esterification catalysts in conjunction with aqueous $H_2O_2$ as an oxidant. However, the process for using this catalyst requires the presence of lower aliphatic hydrocarbon acids such as glacial, formic, acetic and propionic acid as solvents. Under these conditions the reaction times vary from ½ to 4 hours, but at the shorter reaction times it is disclosed that substantial amounts of epoxide result thereby indicating that the reaction proceeds via the peracid route. The only yield disclosed is obtained in connection with tungsten hexachloride in Example 1. This yield is extremely low, i.e. 22%, and includes both half-acetate and diol. When an equivalent of Example 2 of this patent was conducted, the conversion of hydrogen peroxide was found to be 10%, the selectivity to diol was 10%, the selectivity to diacetate was 20% and the diol yield was 1%. Thus, among the major disadvantages of the process described in this patent are the low selectivities to diol and the corrosiveness of metal halides in the presence of glacial acids such as acetic acid.

Japanese Patent Application No. Sho. 54-145604, published Nov. 14, 1979, is directed to a process for hydroxylating olefins in the presence of $OsO_4$, a quaternary ammonium salt such as tetraethylammomium bromide, and a peroxide including organoperoxides and $H_2O_2$ as the oxidant. The use of oxygen as the oxidant is not disclosed nor is the co-presence of co-catalyst I salts as described herein disclosed. Selectivities to glycol of from about 4.5 to about 66% are disclosed. $H_2O_2$ oxidant in combination with $OsO_4$ is known as Milas reagent which can lead to non-selective oxidation of olefins as well as over oxidation. $H_2O_2$ is also substantially more expensive than oxygen or air. Accordingly, the uses of organohydroperoxides as well as $H_2O_2$ as oxidants are each associated with their own disadvantages.

U.S. Pat. No. 2,214,385 discloses the use of hydrogen peroxide and a catalytically active oxide, such as osmium tetroxide, dissolved in an essentially anhydrous, non-alkaline, inert, preferably organic, solvent, to convert, by oxidation, unsaturated organic compounds to useful oxygenated products such as glycols, phenols, aldehydes, ketones, quinones and organic acids. The formation of glycols is achieved by conducting the reaction at temperatures of between several degrees below 0° C. and 21° C. Such low reaction temperatures drastically and disadvantageously, reduce the reaction rate to commercially unacceptable levels. At temperatures greater than 21° C., the formation of aldehydes, ketones, and acids is favored.

U.S. Pat. No. 2,773,101 discloses a method for recovering an osmium containing catalyst such as osmium tetroxide, by converting it to the non-volatile osmium dioxide form, distilling the hydroxylation product, reoxidizing the osmium dioxide to the volatile osmium tetroxide, and then recovering the same by distillation. Suitable oxidizing agents used to re-oxidize the osmium dioxide, include inorganic peroxides such as hydrogen peroxide, sodium peroxide, barium peroxide; organic peroxides, such as t-butyl peroxide or hydroperoxide, benzoyl peroxide; as well as other well known oxidizing agents such as oxygen, perchlorates, nitric acid, chlorine water and the like. As with other methods of the prior art, the above process yields undesirable by-products (see Col. 1, line 55) thus reducing the selectivity of the process.

British Patent Specification No. 1,028,940 is directed to a process for regenerating osmium tetroxide from reduced osmium oxides by treatment of the latter with molecular oxygen in an aqueous alkaline solution. More specifically, it is disclosed that when osmium tetroxide is used by itself as an oxidizing agent, or as a catalyst in conjunction with other oxidizing agents, to oxidize hydrocarbons the osmium tetroxide becomes reduced, and in its reduced form is less active than osmium tetroxide itself. Consequently, by conducting the oxidation reaction in the presence of an alkaline medium and supplying oxygen to the medium throughout the process, the osmium tetroxide is maintained in a high state of activity. The oxidation products disclosed include not only ethylene glycol from ethylene but also organic acids from such compounds as vicinal glycols, olefins, ketones, and alcohols. While the pH of the alkaline medium is disclosed broadly for all possible reactions as varying from 7.5 to 12 for purposes of re-oxidizing reduced osmium tetroxide, the pH employed in the example for preparing ethylene glycol is 9.5. If the pH is too high, a wide variety of products are produced as a result of over oxidation and/or degradation. Thus, the sensitivity of the process to the pH of the medium necessitates rigid pH control which is economically disadvantageous.

U.S. Pat. No. 4,255,596 is directed to a process for preparing ethylene glycol in a homogeneous single-phase reaction medium using ethylbenzene hydroperoxide as the oxidizing agent dissolved in ethylbenzene and osmium tetroxide as the catalyst. The pH of the reaction medium is maintained at about 14 by the presence of tetraalkyl ammonium hydroxide. A small amount of water can dissolve beneficially in the medium to reduce by-product formation and improve selectivity to the glycol.

U.S. Pat. No. 4,049,724 describes the preparation of glycols from alkenes and from unsaturated alcohols in an aqueous system using osmium tetroxide and specifying stable and water-soluble aliphatic hydroperoxides, such as tert-butyl hydroperoxide, while a critical pH of 8 to 12 is maintained by a suitable combination of alkali metal buffering compounds. The preparation of propylene glycol utilizing tert-butyl hydroperoxide is exemplified in the patent at a selectivity based on the hydroperoxide of 45 percent.

None of the aforenoted patents disclose the osmium containing-co-catalytic system described herein.

See also: U.S. Pat. No. 3,317,592 (production of acids and glycols using oxygen as oxidant, $OsO_4$ as catalyst at pH 8-10); U.S. Pat. No. 3,488,394 (discloses hydroxylation of olefins by reacting olefin and hypochlorite in the presence of $OsO_4$); U.S. Pat. No. 3,486,478 (discloses reaction of hypochlorite and olefin in an aqueous medium and in the presence of $OsO_4$ catalyst to hydroxylate the olefin); U.S. Pat. No. 3,928,473 (hydroxylation of olefins to glycols with $O_2$ oxidant, octavalent osmium catalyst (e.g., $OsO_4$), and borates as promoter); U.S. Pat. No. 3,931,342 (discloses a process for recovering glycols from an aqueous solution containing alkali metal borate and osmium compounds (e.g., $OsO_4$); U.S. Pat. No. 3,953,305 (discloses use of $OsO_4$ catalyst for hydroxylating olefins which is regenerated by oxidizing hexavalent osmium with hexavalent chromium and electrochemically regenerating hexavalent chromium); U.S. Pat. No. 4,203,926 (discloses ethylbenzene hydroperoxide as oxidant used in two phase system to hydroxylate olefins in presence of $OsO_4$ and cesium, rubidium and potassium hydroxides); U.S. Pat. No. 4,217,291 (discloses the oxidation of Osmium (III) or (IV) in an ionic complex with oxygen and an alkali metal, ammonium, or tetra (-lower) alkyl ammonium cation to a valency of greater than +5 in the presence of organo hydroperoxides); and U.S. Pat. No. 4,229,601 (discloses the use of cesium, rubidium and potassium hydroxides as promoters for $OsO_4$ catalyst and t-butyl hydroperoxide oxidant for hydroxylating olefins).

SUMMARY OF THE INVENTION

The present invention resides in the discovery that certain heteroaliphatic nitrogen containing compounds referred to herein as co-catalyst II can substantially improve the rate of the direct hydroxylation of olefins to their corresponding diols, e.g. vicinal diols, in a reaction system which employs (a) an osmium compound as a catalyst rather than as a stoichiometric oxidant, (b) a transition metal (i.e. copper) containing compound as a co-catalyst, and (c) molecular oxygen as the oxidant. The present invention represents an improvement over the processes described in commonly assigned U.S. Pat. No. 4,390,739 and U.S. patent application Ser. No. 310,217, filed Oct. 9, 1981, by R. Austin and R. Michaelson.

The direct hydroxylation route of the present invention avoids the formation of an oxirane intermediate that must be hydrolyzed to form the corresponding diol and which can lead to undesirable by-products as is the case of the $H_2O_2$-peracid route to olefin hydroxylation.

Furthermore, the catalytic nature of the present invention is far more cost effective and convenient than osmium stoichiometric routes to olefin hydroxylation.

The accelerating effect of co-catalyst II is quite surprising in the reaction system described herein. For example, in stoichiometric osmium oxide based olefin hydroxylations, one is unconcerned with the reoxidation of stoichiometric osmium oxidant, since once used up it is removed from the reaction system. Consequently, the rate influencing steps in such reactions are the formation of the osmium oxide-olefin cis-ester intermediate and the hydrolysis of the ester. In contrast, in an osmium oxide catalyzed reaction system, the osmium catalyst must go through repeated cycles of reduction and reoxidation. Consequently, the rate of reoxidation of the osmium becomes a significant rate influencing step. Thus, while certain tetriary amines, such as pyridine, are known to accelerate the formation of the cis-ester intermediate in stoichiometric oxidations, it is not known what effect, if any, such amines will have on the overall hydroxylation reaction rate of oxygen based, osmium catalyzed hydroxylations which have been facilitated by a particular transition metal, i.e., copper, co-catalyst. In the environment in which the co-catalyst II rate promoter is employed in the present invention, it is believed that the rate accelerating effect achieved thereby is attributable to interaction with the transition metal of Co-catalyst I rather than with the osmium catalyst.

Accordingly, in one aspect of the present invention there is provided a process for hydroxylating at least one olefinic compound having at least one ethylenic unsaturation which comprises reacting said olefinic compound in the presence of oxygen, water, and a catalyst composition in a manner and under conditions sufficient to convert at least one of said ethylenic unsaturation directly to it corresponding diol, said catalyst composition comprising:

(a) at least one catalytically active osmium containing compound;

(b) at least one transition metal containing Co-catalyst I having an identity and in an amount effective to increase at least one of the rate and selectivity of the hydroxylation reaction relative to its absence; said transition metal being copper; and (c) at least one Co-catalyst II selected from the group consisting of 1,4-diazabicyclo [2.2.2] octane and hexamethylenetetramine in an amount effective to increase the rate of the hydroxylation reaction relative to its absence.

In another aspect of the present invention the aforedescribed process additionally employs a halo-source to further enhance the rate and/or selectivity of the hydroxylation reaction.

DESCRIPTION OF PREFERRED EMBODIMENTS

In accordance with the present invention, at least one olefin containing at least one ethylenic unsaturation is reacted with oxygen in the presence of water and a catalyst composition comprising a catalytically active osmium containing compound, at least one Co-catalyst I as described herein, at least one Co-catalyst II as described herein, and optionally, but preferably, at least one Co-catalyst III, to convert at least one of said ethylenic unsaturation directly to its corresponding diol.

I. Olefin

Olefins which can be hydroxylated in accordance with the present invention contain at least one ethylenic unsaturation and comprise any of the unsaturated aliphatic or alicyclic compounds well known in the art for undergoing such hydroxylation reactions. Typically, such compounds will contain from 2 to about 20 carbons, preferably from 2 to about 10 carbons, and most preferably from 2 to about 5 carbons. Such compounds may be straight or branched chain, mono-olefinic, di-olefinic, or polyolefinic, conjugated or non-conjugated. They may be substituted with such groups as $C_1$ to $C_{10}$ alkenyl, $C_8$ to $C_{14}$ aralkenyl, aryl, preferably aryl of from about 6 to about 14 carbons, alkyl, preferably alkyl of from 1 to 10 carbons, or aralkyl and alkaryl wherein the alkyl and aryl portions thereof are as described above, as well as with functional groups such as hydroxyl, carboxyl and anhydride.

Typical of such olefins are those represented by the structural formula:

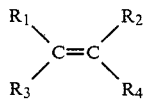

(I)

wherein $R_1$, $R_2$, $R_3$, and $R_4$, which may be the same or different, are selected from the group consisting of hydrogen; substituted or unsubstituted: alkenyl, aralkenyl, alkyl, aryl, alkaryl, and aralkyl hydrocarbyl groups, said hydrocarbyl groups being preferably as defined immediately above; or any two or said $R_{1-14}$ groups together can constitute a cycloalkyl group typically of from about 4 to about 12, preferably from about 5 to about 8 carbons.

Representative olefins which can be hydroxylated and contain at least one ethylenic saturation include: ethylene, propylene, butene-1, butene-2, isobutene, pentene-1, pentene-2, hexene, isohexene, heptene, 3-methylhexene, octene-1, isooctene, nonene, decene, dodecene, tridecene, pentadecene, octadecene, eicosene, docosene, tricosene, tetracosene, pentacosene, butadiene, pentadiene, hexadiene, octadiene, decadiene, tridecadiene, eicosadiene, tetracosadiene, cyclopentene, cyclohexene, cycloheptene, methylcyclohexene, isopropylcyclohexene, butylcyclohexene, octylcyclohexene, dedecylcyclohexene, acrolein, acrylic acid, 1,2,3,4-tetrahydrophthalic anhydride, allyl alcohol, methyl methacrylate, styrene, cholestrol, and the like.

The preferred olefins are ethylene, propylene, isobutylene, styrene, allyl alcohol and allyl chloride.

The most preferred olefins are propylene, ethylene, and butenes.

II. Osmium Compound (Catalyst)

In accordance with the present invention, it has been found that the oxidation state of osmium in osmium catalyst as initially added to the reaction mixture is not critical to catalytic activity when the appropriate co-catalyst system is employed as described hereinafter, i.e., any osmium compound as described herein when subjected to hydroxylation conditions as described herein, itself possesses, or is converted under such hydroxylation conditions to a species which possesses, the capability of catalyzing the hydroxylation of olefins with oxygen.

In view of the above, it is possible to flexibly tailor the identity of the osmium compound and co-catalyst system described herein to achieve an extremely efficient catalyst system for hydroxylating olefins with oxygen. In selecting the particular osmium compound for use in the present invention, the volatility and/or toxicity of the compound, and its activity in the system employed will be taken into consideration.

More specifically, included within the scope of osmium compound (the term "osmium compound" is defined herein broadly to also include osmium metal as well as ionic and neutral complexes of osmium and a ligand) which can be employed in the process of the present invention include in their order of preference halogenated osmium compounds, ionic osmium compounds, osmium oxides, osmium complexes, osmium carbonyls, and osmium metal.

Representative halogenated osmium compounds are disclosed in U.S. patent application Ser. No. 310,217, filed Oct. 9, 1981 the disclosure of which is herein incorporated by reference.

For example, osmium-halogen containing compounds include osmium halides and osmium oxy halides, and complexes thereof, (all of the above being referred to herein collectively as osmium-halides) such as those represented by the structural formulae: $Os(X)_n$ (e.g., $OsX_3$, $OsX_4$, and $OsX_5$); $Os(OH)X_3$; $OsOX_4$; $OsO_3X_2$; $OsONX_4$; $(M)_{n'}[OsX_6]^{-2}$; $(M)_{n'}[OsO_2X_4]^{-2}$; $M^{+1}[Os(OH)X_5]^{-1}$; $(M)_{n'}[OsO_4X_2]^{-2}$; $(M)_{n'}[OsO_2(OH)_2X_2]^{-2}$; $(M)_{n'}[OsNX_5]^{-2}$; and mixtures thereof: wherein X is halogen independently selected from the group consisting of F, Cl, Br and I; n is an integer which can vary from 1 to 6 (e.g. 3 to 5), M is a cation including cations of alkali metals, (e.g., Li, Na, K, Rb, Cs, Fr), alkaline earth metals (e.g., Be, Mg, Ca, Sr, Ba, Ra), ammonium (i.e., $NH_4^+$), tetrahydrocarbyl ammonium (e.g. $(R)_4N^+$) are tetrahydrocarbyl phosphonium (e.g. $(R)_4P^+$) said tetrahydrocarbyl groups being as defined in connection with Group 5 Co-catalysts III discussed below; and n' is a number which is selected in conjunction with the valence of cation M to achieve a neutral complex; preferably n' is 1.

Representative examples of such compounds include $OsF_3$, $OsCl_3$, $OsBr_3$, $OsI_3$, $OsF_4$, $OsCl_4$, $OsBr_4$, $OsI_4$, $OsF_5$, $Os(OH)Cl_3$, $Os(OH)F_3$, $OsOF_4$, $OsOCl_4$, $OsO_3F_2$, $OsONCl_4$, $K_2[OsCl_2Br_2I_2]$, $(NH_4)_2[OsF_6]$, $Ca[OsI_6]$, $Li_2[OsO_2Cl_4]$, $(CH_3CH_2)_4N[Os(OH)Cl_5]$, $Mg[OsO_4F_2]$, $Na_2[OsO_2(OH)_2Cl_2]$, $Ba[OsNCl_5]$, $K_2[OsNCl_5]$, $(CH_3CH_2)_4P[Os(OH)Br_5]$, $Mg[OsNBr_5]$, Na$_2$[OsO$_2$(OH)$_2$Br$_2$], Ba[OsNCl$_5$], K$_2$[OsNCL$_5$], K$_2$[OsNBr$_5$], and mixtures thereof.

The preferred compounds of this class are those having a boiling point at atmospheric pressure of typically greater than about 130° C., preferably greater than about 150° C., and most preferably greater than about 175° C.

The most preferred compounds are those represented by the sturctural fromula OsX$_3$ such as OsBr$_3$.

In selecting the appropriate halogen for the osmium-halide the order of preference in terms of activity is Br, Cl, I and F.

The compounds having the formula Os(X)$_n$ can be prepared by the general methods described in "Advanced Inorganic Chemistry" by Cotton and Wilkinson (hereinafter Cotton and Wilkinson), p. 909 (4th ed. 1980).

Compounds having the formula OsOX$_4$ and OsO$_3$X$_2$ can be prepared by the method described in the "J. Inorganic Nuclear Chemistry" by Hepworth and Robinson, Vol. 4, p. 24 (1957).

Compounds having the formula Os(OH)X$_3$ can be prepared by the method described in "Comprehensive Inorganic Chemistry", Trotman-Dickenson (ed.) vol. 3, p. 1217 (1973).

Compounds having the formula OsONX$_4$ can be prepared by the method described in "Comprehensive Inorganic Chemistry" described above at vol. 3, p. 1233.

Compounds having the formula $(M)_{n'}[OsX_6]^{-2}$ can be prepared by the general method described in Cotton and Wilkinson, p. 919.

Compounds having the formula $(M)_{n'}[OsO_2X_4]^{-2}$ can be prepared by the general method described in Cotton and Wilkinson, p. 917.

Compounds having the formula $M^{+1}[Os(OH)X_5]^{-1}$ can be prepared by the general method described in "Z. Anorg. Allgen. Chem" by Krauss and Wilken (hereinafter Krauss and Wilken) vol. 137, p. 349 (1924).

Compounds having the formula $(M)_{n'}[OsO_4X_2]^{-2}$ can be prepared by the method described in Krauss and Wilken, vol. 145, p. 151 (1925).

Compounds having the formula $(M)_{n'}[OsO_2(OH)_2X_2]^{-2}$ can be prepared by the method described in Cotton and Wilkinson, p. 914.

Compounds having the formula $(M)_{n'}[OsNX_5]^{-2}$ can be prepared by the method described in "Inorganic Synthesis", by E. G. Rochow, vol. 6, p. 204 (1960).

The disclosures of all of the above references illustrating the methods of preparation of the aforenoted osmium-halide compounds are herein incorporated by reference.

The osmium carbonyl containing compounds suitable for use herein are described in U.S. patent application Ser. No. 420,137, filed Sept. 20, 1982, the disclosure of which is herein incorporated by reference.

More spcifically, the term osmium carbonyl compound is defined herein broadly to also include, in addition to compounds, ionic and neutral complexes of osmium with at least one carbonyl ligand and optionally other ligands such as phosphines, hydride, halide and the like as described hereinafter.

Thus, suitable osmium carbonyl compounds include Os(CO)$_5$, Os$_2$(CO)$_9$, Os$_3$(CO)$_{12}$, Os$_5$(CO)$_{16}$, Os$_6$(CO)$_{18}$, Os$_7$(CO)$_{21}$, and Os$_8$(CO)$_{23}$.

Osmium carbonyl complexes suitable for use as the osmium carbonyl catalyst include those represented by the formulae: $[Os(CO)X'_5]^{-2}$, $[Os(CO)_2X'_4]^{-2}$, $[Os(CO)_3X'_3]^{-1}$, $[Os(CO)_4X']^{-2}$, and $Os(X'')_a(CO)_b(Y)_c(PR'_3)_d$, wherein X' is halogen, preferably bromine, X'' is independently selected from hydrogen (i.e. hydride), cyclopentadienyl (CPD), and halogen (preferably bromine), Y is independently selected from NO, NH$_3$, and N$_2$, R' is a hydrocarbyl group independently selected from alkyl, typically alkyl of from about 1 to 10, preferably from about 1 to 5, most preferably from about 1 to 3 carbons, aryl, typically aryl of from about 6 to about 14, preferably from about 6 to about 10, most preferably about 6 carbons, alkaryl and aralkyl wherein the alkyl and aryl groups thereof are as defined immediately above, "a" and "c" represent numbers of from 0 to about 3, "b" represents a number of at least 1, "d" represents a number of 2 or 3 and the sum of a, b, c, and d is selected in conjunction with the valence of Os to achieve a neutral complex.

Representative examples of suitable osmium carbonyl complexes include $[Os(CO)Cl_5]^{-2}$, $[Os(CO)I_5]^{-2}$, $[Os(CO)_2Br_4]^{-2}$, $[Os(CO)_2I_4]^{-2}$, $[Os(CO)_3I_3]^{-1}$, $[Os(CO)_3Cl_3]^{-1}$ $[Os(CO)_4I]^{-2}$, $[Os(CO)_4Cl]^{-2}$, Os($\pi$-CPD)$_2$(CO)(P$\phi_3$)$_2$, OsCl$_2$(CO)(P$\phi_3$)$_2$, Os(CO)$_3$(P$\phi_3$)$_2$, OsHCl(CO)(P$\phi_3$)$_3$, OsI(CO)(NO)(P$\phi_3$)$_2$, OsHCl(CO)(PEt$_2\phi$)$_3$, OsI$_2$(CO)(P$\phi_3$)$_2$, OsHI(CO)(P$\phi_3$)$_3$, and mixtures thereof; "Et" representing ethyl, "$\phi$" representing phenyl, and $\pi$-CPD representing pi-bonded cyclopentadienyl.

The preferred osmium carbonyl compound is Os$_3$(CO)$_{12}$.

The aforenoted osmium carbonyl compounds can be prepared by conventional methods as described in "Inorganic Synthesis", Vol. 13, p. 92 (F. A. Cotton ed. 1972); "Quarterly Reviews", Vol. 24, p. 498 (1970); and "Advanced Inorganic Chemistry", Cotton and Wilkinson, p. 1000 to 1017 (3rd ed. 1972).

Representative osmium oxides include OsO$_2$, OsO$_3$, OsO$_4$, and mixtures thereof. The preferred osmium oxide is OsO$_4$.

Representative ionic osmium oxide compounds are described in U.S. Pat. No. 4,217,291 the disclosure of which is herein incorporated by reference. These ionic osmium compounds can be represented by the formula:

$$M'_xOsO_y \qquad (II)$$

wherein M' is a cation of an alkali or alkaline earth metal, ammonium, or tetraalkyl ammonium, preferably tetraalkyl ammonium in which the alkyl group has from about 1 to about 5 carbons, and x and y are numbers such that $2y-x$ is the valence of the osmium in any compound defined by this formula. While the preferred ionic osmium compounds of this class are the perosmates (M'$_2$OsO$_5$) other ionic osmium compounds such as M'$_2$OsO$_4$ (known as osmates), M'$_2$OsO$_3$, and M'OsO$_2$ can also be employed.

Representative of osmium complexes include those which form with ligands of PR'$_3$ (R' being as described above), amines, nitride, $\pi$-bonded cyclopentadienyl ($\pi$-CPD), and mixtures thereof.

Illustrative osmium phosphine complexes can be represented by the structural formula:

$$Os(X'')_d(Y)_e(PR'_3)_f \qquad (III)$$

wherein X'' is independently selected from hydrogen, (e.g., hydrido) cyclopentadienyl (CPD), and halogen (preferably bromine); Y is independently selected from NO, NH$_3$, and N$_2$; R' is hydrocarbyl group independently selected from alkyl, typically alkyl of from about 1 to about 10, preferably from about 1 to 5, most preferably from about 1 to 3 carbons, aryl, typically aryl of from about 6 to about 14, preferably from about 6 to about 10, most preferably about 6 carbons, alkaryl and aralkyl wherein the alkyl and aryl groups thereof are as defined immediately above, "d" and "e" are numbers of from 0 to about 3, "f" is a number of 2 to 4 (e.g. 2 to 3) and the sum of d, e, and f is selected in conjunction with the valence of Os to achieve a neutral complex.

Representative examples of suitable osmium phosphine complexes include $OsH_2(N_2)(P\phi_3)_3$; $OsH_2(P\phi_3)_4$; $OsCl_2(P\phi_3)_3$; $OsCl_3(NO)(P\phi_3)_2$; $OsCl(NO)(P\phi_3)_2$; $OsCl_2(NH_3)(PEt_2\phi)_3$; $Os(\pi\text{-}CPD)_2(NH_3)(P\phi)_2$, and mixtures thereof; "Et" representing ethyl, "$\phi$" representing phenyl, and $\pi$-CPD representing pi-bonded cyclopentadienyl.

Illustrative osmium amine complexes include aromatic amine complexes illustrated by $[Os(bipy)_3]^{+2}$ wherein bipy is 2,2'-bipyridine, and $[Os(NH_3)_5X]^{+2}$ wherein X is halogen, preferably Br.

Illustrative osmium nitride complexes include $[OsO_3N]^-$; $K[OsO_3N]$; and $OsO_3NC(CH_3)_3$.

Illustrative $\pi$-CPD complexes include $Os(\pi\text{-}CPD)_2$.

Methods for preparing the aforedescribed osmium complexes are conventional and are summarized in Cotton and Wilkinson "Advanced Inorganic Chemistry" pages 1000–1017 (3rd ed. 1972).

The osmium containing compounds are employed in amounts effective to catalyze the hydroxylation reaction. Thus while any effective amount of osmium catalyst will suffice, it is contemplated that such effective amounts constitute, when the osmium compound is in unsupported form, a ratio of the moles of osmium in the osmium compound to moles of ethylenic unsaturation to be hydroxylated in contact with said osmium compound of typically from about $1\times10^{-1}$:1, to about $1\times10^{-10}$:1, preferably from about $1\times10^{-2}$:1 to about $1\times10^{-6}$:1, and most preferably from about $1\times10^{-2}$:1 to about $1\times10^{-5}$:1.

Alternatively, such amounts may be expressed as varying from about 1 to about 10,000, preferably from about 10 to about 5,000, and most preferably from about 50 to about 1,000 ppm, based on the total weight of liquid reaction medium including the weight of olefin and any other additives, solvent, or co-catalysts.

While it has been determined that the hydroxylation reaction is first order in the osmium compound, the high cost of osmium will generally militate against using large amounts of osmium in the reaction system.

III. Support

The aforedescribed osmium containing compounds can be employed in supported or unsupported form. The use of supported osmium compounds for hydroxylation catalysts is described in U.S. Pat. No. 4,413,151, the disclosure of which is herein incorporated by reference, said use being applicable to use in conjunction with the catalyst system described herein.

Accordingly, the material on which the osmium compound is supported can be inorganic or organic but must be insoluble in the reaction mixture under reaction conditions and be capable of physically and/or chemically adsorbing the osmium compound to the extent that it retains a catalytically effective amount of the osmium compound adsorbed thereon.

Representative supports include alkaline earth metal oxides including MgO, CaO, BaO, BeO and SrO; $Sc_2O_3$; $Y_2O_3$; oxides of the Lanthanide series of elements represented by the formula $Ln_2O_3$, wherein Ln represents a lanthanide element (i.e., atomic number 58 to 71); alumina ($Al_2O_3$); silica ($SiO_2$); silica gel; silica-alumina; silicon carbide; titania ($TiO_2$); titania-silica; carbon; activated carbon; $Al_2O_3.B_2O_3$, $SiO_2.B_2O_3$, and mixtures thereof; alkaline earth metal orthosilicates such as $Ca_2SiO_4$, $Mg_2SiO_4$; heteropolyanions such as heteropoly tungstates, heteropoly molybdates (e.g., $Na_3PMO_{12}O_{40}$) and the like; and insoluble halogen salts such as $Hg_2I_2$, $HgI_2$, and $PbI_2$.

Another class of suitable supports include ionic materials onto which the osmium compound can be adsorbed. Included within the scope of ionic supports are zeolites, and ionic polymeric compounds.

(IV) Co-catalyst System (a) Co-catalyst I

Co-catalyst I is a term used to refer to at least one organic or inorganic transition metal, i.e., copper, containing compound including complexes. Such copper compound will typically be initially employed as a salt having an anion and a cation, wherein the anion of said salt includes halide, pseudo halide, carboxylate, aryloate, and aryolate and other anions described hereinafter.

The cation transition metal of said Co-catalyst I salts is copper.

More specifically, the anion of Co-catalyst I includes:

(a) halide ions, in their order of preference as follows: bromide, chloride, iodide, fluoride;

(b) carboxylate anions, typically carboxylate anions represented by the structural formula:

wherein $R_5$ is selected from the group consisting of substituted and unsubstituted: alkyl, typically about $C_1$ to about $C_{10}$ alkyl, preferably about $C_1$ to about $C_5$ alkyl, and most preferably about $C_1$ to about $C_3$ alkyl; cycloalkyl, typically about $C_4$ to about $C_{20}$ cycloalkyl, preferably about $C_5$ to about $C_{15}$ cycloalkyl, and most preferably about $C_6$ to about $C_{10}$ cycloalkyl; and aralkyl, typically aralkyl wherein the aryl group thereof is as defined in connection with Ar of structural formula V below and the alkyl group thereof is as defined immediately above; said $R_5$ substituents including hydroxyl; halide (i.e., F, Cl, Br, and I); ether groups, typically ether groups represented by the structural formulae $-O-R_6$, and $-R_7-O-R_6$ wherein $R_6$ and $R_7$ are independently selected from the group consisting of alkyl, typically about $C_1$ to about $C_{10}$ alkyl, preferably about $C_1$ to about $C_5$ alkyl and most preferably about $C_1$ to about $C_3$ alkyl; and ester groups, typically ester groups, represented by the structural formulae

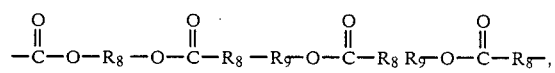

wherein $R_8$ and $R_9$ which may be the same or different are as defined in connection with $R_6$ and $R_7$;

(c) aryloate anions, typically aryloate anions represented by the structural formula:

wherein Ar is selected from the group consisting of substituted and unsubstituted: aryl, typically $C_6$ to about $C_{14}$ aryl, preferably $C_6$ to about $C_{10}$ aryl (e.g., $C_6$ aryl) and alkaryl, typically alkaryl wherein the alkyl group is as defined above in connection with $R_5$ being alkyl, and the aryl group thereof is as defined above, and wherein said substituents on the Ar group are as defined above in connection with $R_5$;

(d) aryolate anions, typically aryolate anions represented by the structural formula:

$$(Ar)O^- \quad (VI)$$

wherein Ar is as described above in connection with structural formula IV, and preferably is aryl; and (e) pseudo halide anions, defined herein to be selected from the group consisting of $SCN^-$, $CN^-$, $SeCN^-$, $TeCN^-$, $OCN^-$, and $CNO^-$; and (f) anions selected from the group consisting of $NO_3^-$, $R_{10}S^-$, $HS^-$, $R_{10}Se^-$, $HSe^-$, $HTe^-$, and $R_{10}Te^-$, $R_{10}$ being alkyl typically about $C_1$ to about $C_{10}$ alkyl, preferably $C_1$ to $C_5$ alkyl.

In short, the Co-catalyst I, when employed as a salt, can be a single salt, or a mixture of salts and said salts can comprise any of the aforenoted transition metal cations associated with any of the aforenoted group (a)–(f) anions.

Representative examples of Co-catalyst I salts include $CuF_2$, $CuBr_2$, $CuI_2$, $CuCl_2$, $CuI$, $CuCl$, $CuBr$, $CuF$, copper acetate, copper naphthoate, copper benzoate, copper propanoate, copper nitrate, copper 4-ethyl benzoate, copper 4-butyl benzoate, copper decanoate, copper hexanoate, copper phthalocyanine, copper 2-(methoxymethyl) acetate, copper 3-(ethoxy)propanoate, copper 4-(propoxy carbonyl)-butanoate, copper 3-(propyl carbonyl oxy)propanoate, copper 2-(methyl carbonyloxy methyl)acetate, copper 4-(ethoxy carbonyl methyl)butanoate, copper 4-(ethoxy methyl) benzoate, copper 3-(propoxy) naphthoate, copper 4-(ethoxy carbonyl)benzoate, copper 2-(hydroxy)acetate, copper 2-chloro propanoate, copper 4-(bromo) benzoate, copper 4-(hydroxy) benzoate, copper phenolate, copper naphtholate, copper 4-chloro phenolate, copper 5-(hydroxy) naphtholate, $Cu(CN)_2$, $Cu(SeCN)_2$, $Cu(TeCN)_2$, $Cu(OCN)_2$, $Cu(CH_3S)_2$, $Cu(CH_3CH_2S)_2$, $Cu(HS)_2$, $Cu(CH_3-CH_2-CH_2-Se)_2$, $Cu(HSe)_3$, $Cu(HTe)_2$, $Cu(CH_3Te)_2$, and mixtures thereof.

The preferred Co-catalyst I salts include copper: bromide, chloride, iodide, nitrate and acetate.

The amount of Co-catalyst I employed in the reaction system is related to the amount of osmium in contact with reaction mixture. Thus, while any amount of Co-catalyst I effective to enhance the rate and/or selectivity of the hydroxylation reaction relative to its absence can be employed, it is contemplated that such effective amounts constitute a mole ratio of osmium to the transition metal of Co-catalyst I in the reaction system in contact with the olefin, of typically from about 1:1000 to about 1:1, preferably from about 1:500 to about 1:5, and most preferably from about 1:50 to about 1:10.

(b) Co-catalyst II

Co-catalyst II is defined herein to be at least one cycloaliphatic amine compound described hereinbelow capable of improving the rate of the hydroxylation reaction when employed in the presence of the osmium compound catalyst, at least one Co-catalyst I, and oxygen.

Co-catalyst II is selected from the group consisting of 1,4-diazabicyclo [2.2.2] octane (referred to herein as DABCO) represented by the structural formula:

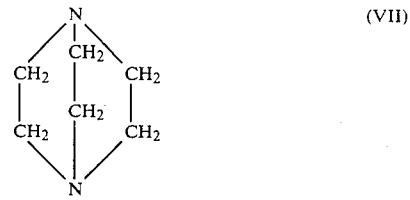

and 1,3,5,7-tetraazatricyclo [3.3.1.1] decane also known as hexamethylenetetramine (HMTA) and represented by the structural formula:

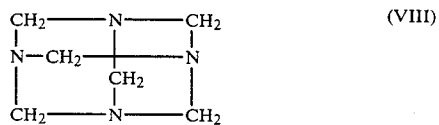

and mixtures thereof.

The amount of Co-catalyst II employed in the reaction system will affect the performance thereof. While any amount effective to increase the rate of the hydroxylation reaction can be employed, such amounts will generally constitute a ratio of moles of Co-catalyst II to the moles of the transition metal employed as Co-catalyst I of typically from about 1:1 to about 15:1, preferably from about 1:1 to about 10:1, and most preferably from about 1:1 to about 8:1.

The reaction mixture will comprise typically less than 50%, preferably less than 15%, and most preferably less than 5%, by weight of Co-catalyst II, based on the total weight of the liquid contents of the reaction mixture.

(C) Co-catalyst III

Co-catalyst III is a term used herein to describe at least one material, typically employed in an organic or inorganic salt form, which functions in conjunction with Co-catalysts I and II to further improve the rate and/or selectivity of hydroxylation reaction. The use of Co-catalyst III is optional although preferred, particularly with respect to a halide containing Co-catalyst III.

Suitable promoters or Co-catalysts III include alkali (e.g., Li, Na, K, Rb, Cs, and Fr), and alkaline earth metal (e.g., Be, Mg, Ca, Sr, Ba, and Ra): halides, oxides and/or hydroxides, carboxylates, aryloates, aryolates and pseudo halides; tetra hydrocarbyl ammonium: hydroxides, halides, carboxylates, aryloates, and aryolates; tetra hydrocarbyl phosphonium: hydroxides, halides, carboxylates, aryloates, aryolates; hydrogen halides; halogenated hydrocarbons such as alkyl, aryl, aralkyl, alkaryl and cycloalkyl halides; Group III-b (i.e., B, AL, Ga, In, Tl), IV-b (i.e. Si, Ge, Sn, Pb), V-b (i.e., N, P, As, Sb, Bi) and VI-b (i.e., S, Se, Te, Po) halides; and the halogens $F_2$, $Cl_2$, $I_2$, $Br_2$.

More specifically, suitable alkali and alkaline earth metal halide Co-catalysts III (referred to herein as Group I Co-catalysts III) include the Li, Na, K, Rb, and Cs bromides, iodides, chlorides and fluorides; and Mg, Ca, Sr, and Ba, bromides, iodides, chlorides, and fluorides and mixtures thereof. Preferred Group 1 co-catalysts include the Na, K, Rb, Cs, Mg and Ca halides, particularly bromides.

Suitable alkali and alkaline earth metal hydroxide or oxide co-catalysts (referred to herein as Group 2 co-catalysts III) include LiOH, NaOH, KOH, RbOH, CsOH, Ca(OH)$_2$, Ba(OH)$_2$, Mg(OH)$_2$, the corresponding oxides thereof, and mixtures thereof.

Preferred Group 2 Co-catalysts III include the Na, K, Rb, Mg and Ca hydroxides.

Suitable alkali and alkaline earth metal: carboxylate, aryloate, and aryolate co-catalysts (referred to herein as Group 3 Co-catalysts III) include those which possess as anions respectively:

(a) carboxylate anions represented by the structural formula:

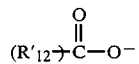   (IX)

wherein R'$_{12}$ can be substituted or unsubstituted: alkyl, typically alkyl of from about 1 to about 10 carbons, preferably about 1 to about 5 carbons, and most preferably about 1 to about 3 carbons, cycloalkyl, typically cycloalkyl of from about 4 to about 20, preferably from about 5 to about 15, and most preferably from about 6 to about 10 carbons, or aralkyl, typically aralkyl wherein the aryl group thereof is as defined in connection with Ar'— of structural formula (X) below and the alkyl group thereof is as defined immediately above; said R'$_{12}$ substituents including: hydroxy; halide (i.e., F, Cl, Br, and I); ether groups represented by the structural formulae —O—R$_6$ and —R$_7$—O—R$_6$ wherein R$_6$ and R$_7$ are independently as described in connection with formula (IV) above; and ester groups represented by the structural formulae:

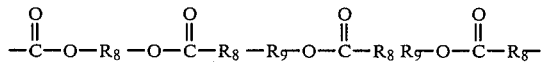

wherein R$_8$ and R$_9$ which may be the same or different are as defined in connection with formula (IV) above and mixtures thereof.

(b) aryloate anions represented by the structural formula:

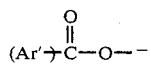   (X)

wherein Ar' is selected from the group consisting of substituted and unsubstituted: aryl, typically aryl of from about 6 to about 14 carbons, preferably from about 6 to about 10 carbons, (e.g., 6 carbons), and alkaryl, typically alkaryl wherein the alkyl group is from about 1 to about 6 carbons, preferably from about 1 to about 3 carbons, and the aryl group thereof is as defined immediately above, and wherein said substituents on the Ar' group are as defined above in connection with R'$_{12}$; and (c) aryolate anions represented by the structural formula:

   (XI)

wherein Ar' is as described above in connection with structural formula (X) and preferably is aryl.

Illustrative examples of such Group 3 Co-catalysts III include: sodium acetate, potassium acetate, calcium acetate, cesium acetate, magnesium acetate, potassium ethanoate, sodium propanoate, magnesium butanoate, strontium pentanoate, sodium benzoate, potassium benzoate, magnesium benzoate, calcium benzoate, sodium naphthoate, potassium naphthoate, beryllium naphthoate, sodium 4-(6-methyl-2-naphthyl)-pentanoate, potassium 3-(7-methyl-1-naphthyl)-propanoate, magnesium 2-(4-propyl-1-benzyl)-ethanoate, calcium phenolate, sodium naphtholate, potassium naphtholate, sodium 3-(ethoxy)-propanoate, potassium 4-(propoxycarbonyl) butanoate, calcium 3-(propylcarbonyloxy)-propanoate, magnesium 2-(methylcarbonyloxymethyl)-acetate, beryllium 4-(ethoxy-carbonylmethyl)-butanoate, cesium 4-(ethoxymethyl)-benzoate, sodium 3-(propoxy)-naphthoate, potassium 4-(ethoxy carbonyl)-benzoate, barium 2-(hydroxy)-acetate, rubidium 2-chloropropanoate, magnesium 4-bromobenzoate, magnesium phenolate, and mixtures thereof.

Preferred Group 3 Co-catalysts III include the Na, K, Rb and Cs acetates.

Suitable alkali and alkaline earth metal pseudo halide Co-catalysts III (referred to herein as Group 4 Co-catalysts III) include those which possess pseudo halide anions selected from the group consisting of: SCN$^-$, SeCN$^-$, TeCN$^-$, OCN$^-$, and CNO$^-$, and mixtures thereof.

Illustrative examples of such Group 4 Co-catalysts III include NaSCN, NaSeCN, KSeCN, CsSeCN, NaTeCN, KTeCN, NaOCN, NaCNO, KOCN, KCNO, CsOCN, CsCNO, CsTeCN, Mg(SeCN)$_2$, Ca(TeCN)$_2$, Ca(OCN)$_2$, Ca(CNO)$_2$ and mixtures thereof.

Preferred Group 4 Co-catalysts III include the Na, K, Rb and Cs thiocyanates.

Tetrahydrocarbyl ammonium or phosphonium salt co-catalysts (referred to herein as Group 5 Co-catalysts III) possess a cation and an anion. The respective cations can be represented by the respective structural formula (R)$_4$N$^+$ and (R)$_4$P$^+$ wherein R is a hydrocarbyl group independently selected from the group consisting of substituted and unsubstituted: alkyl, typically alkyl having from about 1 to about 30 carbons, preferably from about 1 to about 20 carbons, and most preferably from about 1 to about 10 (e.g. 1-5) carbons, aryl, preferably aryl having from 6 to 14 carbons, and most preferably from 6 to about 10 carbons, and alkaryl and aralkyl wherein the aryl and alkyl groups thereof are as defined immediately above; said R substituents being as defined in connection with the substituents of R'$_{12}$ described above. Accordingly, the term hydrocarbyl is intended to include both substituted and unsubstituted groups, and mixtures thereof. The anion of the Group 5 Co-catalysts III are selected from the group consisting of hydroxy, halide, pseudo halide, carboxylate, aryloate and aryolate, said pseudo halide, said carboxylate, aryloate, and aryolate anions, being as defined above in connection with the anions of the alkali and alkali metal Co-catalysts III described above.

Illustrative examples of such Group 5 Co-catalysts III include tetramethylammonium bromide, tetraethylphosphonium chloride, tetradecylphosphonium bromide, tetraphenylammonium chloride, tetraphenylphosphonium bromide, dimethyldiethylammonium iodide, methyltriethylphosphonium chloride, tetrabutylammonium, chloride, phenyltrimethylammonium bromide, phenyltrimethylphosphonium chloride, phenyltriethylammonium iodide, phenyltriethylphosphonium chloride, tetraethylammonium hydroxide, tetrabutylammonium hydroxide, tetraethylphosphoniumhydroxide, phenyltriethylammonium hydroxide, phenyltrimethylphosphonium hydroxide, tetraethylammoniumacetate, tetrabutylphosphonium acetate, phenyltriethylammonium acetate, phenyltrimethylphosphonium acetate, tetraethylammonium benzoate, phenyltrimethylphosphonium benzoate, phenyltriethylammonium naphthoate, tetraethylammonium phenolate, tetrabutylphosphonium naphtholate, tetra-2-(methoxy)ethylphosphonium chloride, tetra-4-(propoxymethyl)-phenylammonium bromide, di-3-(methoxycarbonyl)-propyldiethylphosphonium iodide, di-4-(ethylcarbonyloxy)-butyl-dimethyl ammonium chloride, tetra-5-(ethoxycarbonylmethyl)pentylphosphonium bromide, tetra-4-hydroxybutylammonium acetate, tetra-3-chloropropylphosphonium acetate, tetramethylammonium thiocyanate, tetraethylphosphonium selenocyanate, tetra-(4-methylphenyl)ammonium chloride, tetra-(3-phenyl-1-propyl)phosphonium bromide.

Preferred Group 5 Co-catalysts III include the unsubstituted tetra lower alkyl (e.g., $C_1$ to $C_5$ alkyl) ammonium hydroxides, bromides, iodides, chlorides, fluorides, and acetates.

Suitable hydrogen halides (referred to herein as Group 6 Co-catalysts III) include HF, HCL, HBr, and HI.

Preferred Group 6 Co-catalysts III include HI, HBr, and HCl.

Suitable halogenated hydrocarbons (referred to herein as Group 7 Co-catalysts III) are described in commonly assigned U.S. patent application Ser. No. 399,270, filed July 19, 1982, by R. Austin and R. Michaelson, the disclosure of which is herein incorporated by reference including any halogenated hydrocarbon compound, preferably a halogenated hydrocarbon compound, wherein the hydrocarbyl portion is selected from saturated aliphatic, saturated alicyclic, and aromatic.

More specifically, suitable Group 7 Co-catalysts III can be represented by the structural formula:

$$(R_{13})(X)_{n''} \quad \text{(XII)}$$

wherein $R_{13}$ can be inertly substituted or unsubstituted: alkyl, typically alkyl of from about 1 to about 20, preferably from about 1 to about 10, most preferably from about 1 to about 5 carbons, aryl, typically aryl of from about 6 to about 14, preferably 6 to about 10, most preferably 6 carbons, aralkyl and alkaryl wherein the alkyl and aryl groups thereof are as defined immediately above, cycloalkyl, typically cycloalkyl of from about 4 to about 20, preferably from about 5 to about 15, and most preferably from about 5 to about 10 carbon atoms; X is at least one halogen independently selected from the group consisting of F, Cl, Br, and I, and preferably Br and/or I; $n''$ is a number of from about 1 to about 10, preferably from about 1 to about 8 (e.g., 2 to 6), and most preferably from about 1 to about 6 (e.g., 2 to 4); and said $R_{13}$ substituents including hydroxy, ether and ester groups, said ether and ester substituents being as described in connection with $R'_{12}$ of structural formula (IX). The term "inertly substituted" is defined herein to mean any organic or inorganic substituent which is stable under reaction conditions and does not adversely affect the performance of said co-catalyst, relative to the unsubstituted halogenated organic compound.

Representative examples of suitable Group 7 Co-catalysts III include iodomethane, bromomethane, iodoethane, bromoethane, 1,2-dibromoethane, chloroethane, 1,2-dichloroethane, 1-iodopropane, 1-bromopropane, 1-chloropropane, 2-iodo-1-methylethane, 2-bromo-1-methylethane, 2-chloro-1-methylethane, 1-iodobutane, 2-iodobutane, 2-bromobutane, 1-chlorobutane, 2-methyl-2-iodopropane, 2-methyl-2-bromopropane, 1-iodo-1-methylpropane, 1-bromo-1-methylpropane, 1-chloro-1-methylpropane, 1-iodo-1,1-dimethylethane, 1-chloro-1,1-dimethylethane, 1-chloro-1,1-dimethylethane, benzyliodide, phenyliodomethane, phenylchloromethane, phenylbromomethane, 1,2-dichlorobenzene, 2-bromoethanol, 2-chloroethanol, 2-iodoethanol, 1-phenyl-2-iodoethane, 1-phenyl-4,4-dichlorobutane, 1-(1,2-dichloroethyl)-benzene, 1-(1-chloropropyl)-naphthylene and mixtures thereof.

Preferred Group 7 Co-catalysts include iodomethane, bromoethane, 1-bromobutane, 1-iodobutane, 1-bromo-1,1-dimethylethane, 1-iodo-1,1-dimethylethane, 2-iodobutane, 2-bromobutane, 2-methyl-2-iodopropane, 2-methyl-2-bromopropane, 2-bromoethanol, 2-chloroethanol, 2-iodoethanol, and mixtures thereof.

The most preferred Group 7 Co-catalysts III contains bromide and includes 1-bromobutane, bromomethane, 2-bromobutane, 2-methyl-2-bromopropane, 2-bromoethanol, and mixtures thereof.

Representative examples of suitable Group III-b, IV-b, V-B, and VI-b metal halides (according to the periodic chart of Cotton and Wilkinson "Advanced Inorganic Chemistry" [3rd ed. 1972]) referred to herein as Group 8 Co-catalysts III include halides of Al, Ga, In, Tl, Ge, Sn, Pb, P, Si, As, Sb, Bi, S, Se, Te, and Po.

Specific Group 8 metal halides include $AlCl_3$, $GaBr_3$, $TlCl_3$, $SiCl_4$, $SiBr_4$, $PI_3$, $PBr_3$, $SbF_5$, $SbBr_3$, $SbI_3$, $BiCl_3$, $BiBr_3$, $AsI_3$, $AsBr_3$, $AsCl_3$, $SeF_4$, $SeCl_4$, $SeBr_4$, $TeF_4$ and mixtures thereof.

Suitable halogen Co-catalysts III (referred to herein as Group 9 Co-catalysts III) include $F_2$, $Cl_2$, $Br_2$, and $I_2$.

Any of the Co-catalysts III described in each of the aforenoted Group 1 to 9 Co-catalysts III can be employed alone or in conjunction with one or more Co-catalysts III in the same group and/or with one or more of the Co-catalysts III in the remainder of said groups in any amounts effective to increase the rate and/or selectivity of the hydroxylation reaction relative to that observed in their absence.

Accordingly, while any effective amount of Co-catalyst III can be employed, it is contemplated that such effective amounts constitute typically from about 0.1 to about 10,000 mole percent, preferably from about 10 to about 1000 mole percent, and most preferably from about 25 to about 75 mole percent, Co-catalyst III, based on the total number of moles of osmium in the osmium catalyst employed.

When a supported osmium catalyst is employed, it typically will be utilized as a fixed bed through which the reaction mixture containing the Co-catalyst I, II, and III preferably are determined in a supported system based on the volume of reaction mixture in contact with the fixed bed of supported osmium at any given time during the hydroxylation reaction (referred to herein as the "effective volume"), e.g., the aforedescribed mole percents and/or ratio are contained in the effective volume of the reaction mixture.

Illustrative examples of suitable Co-catalyst combinations include $CuBr_2$ and DABCO; $Cu(NO_3)_2$, HMTA and NaBr; $CuCl_2$, DABCO, and NaBr; $CuBr_2$, HMTA, NaBr; copper acetate, DABCO, and tetraethyl ammonium chloride; $CuI_2$, HMTA, and KBr; $Cu(NO_3)_2$, DABCO, and CsBr; CuI, HMTA, and NaBr; and Cu(-NO₃)₂, DABCO, and n-butyl bromide.

In the aforedescribed catalyst composition comprising at least three components, namely, a catalytically active osmium compound, Co-catalyst I and Co-catalyst II, the third component, i.e., Co-catalyst II, unexpectedly substantially improves the rate of reaction for hydroxylating olefins with molecular oxygen relative to its absence. Although the exact mechanism and reason for this effect is not fully understood, it is considered that the results speak positively for themselves. However, the following is offered as an explanation of the mechanism for the observed catalytic effect in connection with the use of osmium tetroxide as the catalytically active osmium compound, although such explanation is not intended to be exhaustive of all possible mechanistic details. It is known that osmium tetroxide adds across the olefin double bond of the compound to be hydroxylated to yield an intermediate cis-ester as follows:

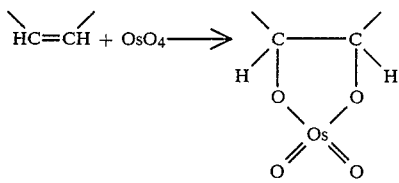

The osmium complex is now formally in the +6 oxidation state. The glycol product can be obtained from this complex by a reductive procedure which is commonly used in the well-known stoichiometric procedure wherein the osmium compound acts as the oxidant, or it can be obtained by oxidative hydrolysis in the presence of an oxidant. This latter route is believed to be operating in the present invention.

Considering this system, it is believed that the copper of Co-catalyst I serves to mediate the reoxidation of osmium by oxygen with concurrent hydrolysis of the glycolate, the copper itself being reduced in the process. The Co-catalyst II, is believed in turn to mediate the reoxidation of the copper through some form of complexed intermediate thereof and/or enhance the solubility of Co-catalyst I in the reaction medium and/or assist in the oxidative hydrolysis of the osmium glycolate. Furthermore, the presence of a halo-moiety in the reaction mixture is believed to facilitate rate of hydrolysis of the glycolate intermediate and may also help to mediate the reoxidation of the transition metal. More specifically, by "halo-" is meant to include halogen in the form of organic and inorganic halide salts or complexes, halogenated hydrocarbons, hydrogen halides as well as the free halogens themselves. Accordingly, it is preferred to provide a halo-source in the reaction mixture. This is typically achieved through the use of a copper halide as Co-catalyst I. If, however, Co-catalyst I is not employed as a halide salt, it is preferred to introduce a halo-source through an alternative means. This can easily be achieved through the appropriate selection of any halo-containing Co-catalyst III, such as for example those described hereinabove including alkali or alkaline earth metal halides (e.g. Group I Co-catalyst III), tetra hydrocarbyl ammonium or phosphonium halides (e.g., Group 5 Co-catalysts III), hydrogen halides (e.g. Group 6 Co-catalysts III), halogenated hydrocarbons (e.g. Group 7 Co-catalysts III), metal halides (e.g. Group 8 Co-catalysts III) and halogens (Group 9 Co-catalysts III), as well as transition metal halides. The halo-source can also be any of the osmium-halides described in connection with the suitable osmium containing compounds. For economic reasons it may be more desirable to employ an inexpensive halo-source such as NaBr to fulfill the aforedescribed halogen balance rather than use the more expensive osmium halides or transition metal halides for this purpose.

Thus, for optimum performance of the reaction system, it is preferred to establish a balance, in terms of amounts, between osmium in the osmium catalyst, the copper of Co-catalyst I, and halogen in the halo-source present in the reaction mixture. Accordingly, it is contemplated that the mole ratio of Os:copper:halogen in the halo-source, in contact with the olefin to be hydroxylated be controlled to be typically from about 1:1:1 to about 1:100:1000, preferably from about 1:10:15 to about 1:50:500, and most preferably from about 1:15:20 to about 1:40:200. In satisfying this balance any halogen in the halo-source, e.g. the osmium catalyst, or Co-catalysts is taken into consideration.

While the above discussed mechanism relates specifically to the use of OsO₄ as the osmium catalyst, the other osmium containing compounds discussed above will also form cis-ester intermediates which must be hydrolyzed, although these intermediates are not of the same chemical composition. Thus, the Co-catalysts I and II as well as the halo-source are believed to function through similar mechanisms regardless of the form of the osmium compound employed.

Furthermore, in view of the above discussion, it is recommended for best results that the most preferred valence of copper of Co-catalyst I as initially employed be that which represents the highest stable oxidation state thereof, since such metals must be capable of being reduced upon oxidizing the Os⁺⁶. While this is not critical, it avoids the need in some instances to initially oxidize the transition metal in-situ so that it can be reduced.

While the hydroxylation reaction can be conducted in a heterogeneous multiphase system, the preferred mode for conducting the hydroxylation reaction is in a liquid reaction mixture, preferably provided as a homogeneous or substantially homogeneous medium by using an inert organic solvent to dissolve, where possible, whatever components are employed in the catalyst and co-catalyst system and reactants. Partial immiscibility of the solvent with water is acceptable although not preferred. By an inert solvent is meant one which does not undergo oxidation during the course of the reaction.

Suitable inert organic solvents include aliphatic or aromatic alcohols having from 1 to about 10 carbon atoms, preferably tertiary alcohols, aliphatic or aromatic ketones having from 3 to about 10 carbon atoms, aliphatic or alicyclic ethers having from 2 to about 10 carbon atoms, glycols having from 2 to about 10 carbon atoms, N, N-dialkyl amides having from 3 to about 10 carbon atoms, nitriles having from about 2 to about 10 carbons, aliphatic or aromatic sulfoxides having from 2 to about 14 carbon atoms, aliphatic or aromatic sulfones having from 2 to about 14 carbon atoms, and the like. Examples of suitable solvents include methanol, ethanol, propanol, butanol, hexanol, decanol, t-butyl alcohol, t-amyl alcohol, benzyl alcohol, acetone, methylethyl ketone, methylbutyl ketone, acetophenone, ethylene glycol, propylene glycol, diethylene glycol, tetraethylene glycol, dimethyl formamide, diethyl formamide, dimethyl acetamide, dimethyl sulfoxide, diethyl sulfoxide, N,N-butyl sulfoxide, diphenyl sulfoxide, dibenzyl sulfoxide, dimethyl sulfone, diethyl sulfone, tetramethylene sulfone (sulfolane), diphenyl sulfone, acetonitrile, dioaxane, tetrahydrofuran, tetrahydropyran, dioxalane, adiponitrile, N-methylpyrrolidone, and mixtures thereof.

The preferred solvents include those which are substantially or completely miscible with water such as t-butyl alcohol, methanol, as well as glycols and/or polyols derived from the olefin being hydroxylated.

The most preferred solvents are dipolar and aprotic such as sulfolane, acetonitrile, N,N-dimethyl acetamide, N,N-dimethylformamide, N-methylpyrrolidone, adiponitrile, and dimethyl sulfone.

The inert solvent is preferably employed in amounts sufficient to achieve a homogeneous solution with respect to at least the olefin and catalyst and Co-catalyst system. Typically such amounts can vary from about 0 to about 98%, (e.g., 10 to 90%), preferably from about about 10 to about 90%, and most preferably from about 20 to about 80%, by weight, based on the total weight of the reaction mixture.

Water is provided to, and/or is present in, the initial reaction mixture in at least a stoichiometric molar ratio with the molar amount of ethylenic unsaturation to be hydroxylated in the olefin. Such ratios preferably are also present in the reaction mixture at any given time after start-up. Accordingly, water is provided in the reaction mixture at molar ratios, of water to ethylenic unsaturation to be hydroxylated in the olefin of from about 1:1 to about 100:1, preferably from about 1:1 to about 10:1, and most preferably from about 1:1 to about 2:1. Such molar ratios typically can be achieved by controlling the amount of water in the reaction mixture to be from about 2 to about 90%, preferably from about 5 to about 50%, and most preferably from about 10 to about 30%, by weight, based on the total weight of the reaction mixture. Preferably the amount of water employed is less than that which will cause separation of the reaction mixture into an aqueous phase and organic phase.

The amount of water employed within the aforedescribed ranges is also influenced by the amount of $O_2$ in the system. Thus, the mole ratio of $H_2O$ to $O_2$ dissolved in the reaction mixture is typically controlled to be from about 1:1 to about 30:1, preferably from about 1:1 to about 15:1, and most preferably from about 1:1 to about 6:1.

The pH of the reaction mixture during the hydroxylation reaction need not be rigidly controlled although it will preferably not be allowed to drop below about 4, preferably now below about 6. Likewise, the pH of the reaction mixture preferably will not be allowed to exceed about 12 although the process can still be conducted at a pH below 4 and above about 12. Active pH control is generally not needed since the pH of the reaction mixture will typically autogeneously vary between about 4 and 12, preferably between about 5 and 12, and most preferably between about 5 and 8.

Furthermore, it will be understood that the use of oxygen in accordance with the process of the present invention inherently avoids the peracid route of olefin hydroxylation, and assures the direct hydroxylation of the olefin. It is also preferred to conduct the hydroxylation reaction in the absence of any organic carboxylic acid such as acetic or propionic acid to avoid esterification of the diol product.

The primary oxidant employed in the present invention is molecular oxygen. Such oxygen can be added as a pure oxygen or as part of an oxygen containing gas such as air or some other oxygen containing gas having one or more inert compounds such as $CO_2$ or $N_2$ present therein. Generally, the oxygen containing gas is present within, preferably dissolved in, the reaction mixture in amounts sufficient to achieve hydroxylation of the olefin.

Accordingly, the molar ratio of oxygen to olefin ethylenic unsaturation can vary widely but for safety reasons it is preferably maintained outside explosive limits.

For example, when hydroxylating ethylene or propylene, if oxygen is in excess of stoichiometry, the ratio typically will be 98 weight % oxygen or more and 2% or less of the olefin. Preferably, however, the olefin is employed in excess, preferably large excess, of stoichiometry, and the oxygen concentration of the oxidizing gas typically will be about 10 mole % oxygen and about 90 mole % olefin. When oxygen is in excess of stoichiometry, olefin can be added as the reaction proceeds. On the other hand, where the olefin is in excess of stoichiometry, oxygen can be added during the reaction as the oxygen is consumed.

Accordingly, in view of the above, the oxygen containing gas preferably is dissolved in the reaction mixture in an amount sufficient to achieve a molar ratio of ethylenic unsaturation to be hydroxylated in the olefin to oxygen in excess of 1:1, typically up to as high as 100:1; and outside the explosive limits of the reaction mixture. It is to be noted, that when either olefin or $O_2$ is employed in substantial excess of stoichiometry for safety reasons the conversion in a batch process will necessarily be very low if based on the component present in large excess. This is not a problem in a continuous process since unreacted components are recycled.

The hydroxylation reaction is typically conducted at temperatures of from about 40° to about 250° C., preferably from about 60° to about 200° C., and most preferably from about 80° to about 170° C. to achieve high selectivities for the hydroxylated olefin.

At temperatures greater than the aforenoted ranges, the reaction rate increases substantially but this usually occurs at the expense of a reduction in selectivity. At very low reaction temperatures, e.g., below about 0° C., the reaction rate decreases to a commercially undesirable degree. Accordingly, while the reaction temperature is not critical and can vary over a wide range, one normally would not operate at temperature extremes outside the aforenoted ranges. Furthermore, since it is preferred to conduct the hydroxylation reaction in the liquid phase, the reaction temperature is typically selected in conjunction with the reaction pressure to achieve this goal.

For the production of ethylene glycol, propylene glycol or any glycol derived from any unsaturated gaseous olefin, the latter may be bubbled through the reaction mixture containing the components described herein or it may be introduced under pressure. Likewise with the oxygen containing gas. However, it is preferred that the reaction takes place in the liquid phase. Consequently, sufficient pressure is preferably employed to maintain the gaseous reactants (i.e., olefin and oxygen) in the liquid phase and/or to dissolve the gaseous reactants into the liquid reaction mixture.

Although the magnitude of the pressure is not critical, it determines the amount of the gaseous reactants that are present in the reaction mixture and therefore affects the rate of reaction. Accordingly, the total pressure of the gases in contact with the reaction mixture is typically controlled to be from about 200 to about 2000 psig, preferably from about 300 to about 1500 psig, and most preferably from about 300 to about 700 psig at the aforenoted reaction temperatures. The partial pressure of each reactant gas, i.e., olefin and oxygen, can be controlled to achieve the aforenoted molar ratios. When the reactant olefin gas is ethylene, the partial pressure (at reaction temperatures) thereof is typically controlled to be from about 100 to about 2000 psig, preferably from about 200 to about 1500 psig, and most preferably from about 300 to about 1200 psig; while when propylene is the reactant olefin, the partial pressure (at reaction temperatures) thereof is typically controlled to be from about 100 to about 2000 psig, preferably from about 200 to about 1500 psig, and most preferably from about 300 to about 1000 psig.

When the olefin reactant is a liquid or is dissolved in the reaction mixture under pressure, its concentration in the reaction mixture typically will vary from about 1 to about 90%, preferably from about 20 to about 80%, and most preferably from about 20 to about 60%, by weight, based on the total weight of the reactant mixture.

In carrying out the invention, olefin, water, oxidant, osmium catalyst, co-catalysts, and optional inert solvent are brought into contact in a manner and under conditions sufficient to hydroxylate the olefin, i.e., to directly convert at least one of the ethylenic unsaturations possessed thereby to its corresponding diol.

Accordingly, the hydroxylation reaction can be performed as a batch reaction, as a continuous reaction or as a semi-continuous reaction. In the batch reaction, the osmium catalyst is charged into the reaction vessel as a solution in the inert solvent along with the Co-catalyst I, Co-catalyst II, optional Co-catalyst III, water, and olefin if in liquid form. The reaction vessel is then pressurized with oxygen and olefin if in gaseous form. It may be desirable to heat the liquid reaction mixture to reaction temperature prior to pressurizing with the reactant gases. The reaction is allowed to proceed to the desired degree of completion.

In the continuous process, the components can be introduced into the inlet of an elongated reactor at a rate such that substantially complete reaction will have taken place by the time the reaction mixture reaches the reactor outlet. The reaction can be carried out in a semi-continuous manner by metering the reactant mixture components into a series of two or more tank reactors at the appropriate rate to maintain the reactor liquid level.

Additionally, the process may be run in either of the aforementioned modes by altering the reaction conditions, and/or, the reactant, solvent, catalyst, and co-catalysts concentrations during the course of the reaction. Thus, the process may be run by changing the temperature, pressure, catalyst concentration, oxidant concentration, and/or olefin concentration.

The spent reaction mixture after removal of unreacted olefin is a solution of product glycol, by-products if any, solvent, water, and catalyst system components. The volatile components are distilled out of the reaction mixture into various fractions leaving non-volatile catalyst system components in the still. The product glycol is then separated from the high boiling distillate.

If the hydroxylation reaction is to be conducted using the supported osmium catalyst, this is typically achieved in fixed bed or slurry form. In the fixed bed mode, the liquid reaction mixture, preferably a homogeneous reaction mixture, is prepared comprising oxidant, co-catalysts, water and olefin and the reaction mixture is passed, preferably continuously, through a fixed bed reactor containing the supported catalyst at reaction temperature and at a rate such that substantially complete reaction will have taken place by the time the reaction mixture reaches the reactor outlet. A variety of fixed bed reactors will be found to be useful and multiple tube heat exchanger type of reactors are satisfactory. In the slurry mode, a reaction mixture containing the above-described components and suspended supported osmium catalyst is charged into a reactor vessel along with olefin and the reaction is allowed to proceed to completion. In a continuous slurry mode, the reaction mixture components can be introduced into the inlet of an elongated reactor adapted to retain, e.g., by filtration, the slurried supported catalyst at a rate such that substantially complete reaction will have taken place by the time the reaction mixture reaches the reactor outlet. The slurry mode can also be carried out in a semi-continuous manner by metering the reactant mixture components into a series of two or more tank reactors adapted as described above at the appropriate rate to maintain the reactor liquid level.

The following examples are given as specific illustrations of the claimed invention. It should be understood, however, that the invention is not limited to the specific details set forth in the examples. All parts and percentages in the examples as well as in the remainder of the specification are by weight unless otherwise specified.

Unless otherwise specified, in the following examples, selectivity, yield, and conversion are calculated as follows:

$$\% \text{ Selectivity} = \frac{\text{Moles of glycol formed}}{\text{Moles of oxygenated product formed}} \times 100$$

$$\% \text{ Conversion} = \frac{\text{Moles of oxygenated product formed}}{\text{Moles of olefin charged}} \times 100$$

$$\% \text{ Yield} = \frac{\% \text{ Conversion} \times \% \text{ Selectivity}}{100}$$

COMPARATIVE EXAMPLE 1

The following Comparative Example omits Co-catalyst II therefrom and is intended to act as a blank against which the following examples can be compared.

Two solutions were prepared as follows: A 30 ml mixture of 80% sulfolane and 20% (V/V) water was prepared and 0.19 mmoles of $OsO_4$ were dissolved therein to form Solution 1. To a 50 ml sulfolane/water (4:1 V/V) mixture was added and dissolved 5 mmoles of $CuBr_2$ to form Solution 2. Solution 1 was then added to a stirred 300 cc autoclave, equipped with a gas dispersing jet followed by Solution 2 with stirring. Thirty grams of propylene were then charged to the reactor. The stirred solution was then heated to 110° C. and 50 mmoles of molecular oxygen charged thereto. A total pressure of 870 psig was recorded. The reaction was allowed to proceed for 20 minutes measured from completion of the $O_2$ addition during which time a 20 psig pressure drop was observed. The mixture was then quickly cooled and the pressure released. A brown, turbid solution (pH 3.5) was obtained from the reactor and analyzed by gas chromatography (5% SP-1000 on Supelcoport) and showed the production of 16 mmoles of propylene glycol. This corresponds to a 16% yield of propylene glycol based on oxygen charged. Minor amounts of acetone 1,2-dibromopropane, and bromopropanol were also produced. The results are summarized at Table 1, Run 1.

EXAMPLES 1-2

The following Examples 1 and 2 are provided to illustrate the performance of the two types of Co-catalysts II.

Thus, the procedures of Comparative Example 1 were repeated with the exception that 12.4 mmoles of a different Co-catalyst II for each of Examples 1 and 2 were added to Solution I to hydroxylate propylene. The results as well as the identity of each Co-catalyst II are summarized at Table 1, Runs 2 to 3.

COMPARATIVE EXAMPLES 2 TO 11

In accordance with the procedure of Example 1, 12.4 mmoles of a different aromatic amine, imidazole, or aliphatic tertiary amine, outside the scope of the Co-catalyst II of the present invention, for each of Comparative Examples 2 to 11, was employed in the hydroxylation of propylene. The results as well as the identity of each amine employed is summarized at Table 2, Runs 4 to 13.

12), 4,5-diazaphenanthrene (Run 13), 1,3-diazabenzene (Run 9), benzimidazoline (Run 8), quinuclidine (Run 5), 2,2'-bipyridine (Run 6) and 1,4-diazabenzene (Run 7) actually decreased the reaction rates relative to their absence and/or inhibited the reaction completely. Such data are evidence that the Co-catalysts II described herein operate through a mechanistic route quite different than that observed for tertiary amines in conjunction with conventional tertiary amine promoted stoichiometric osmium oxidations of olefins. For example, not only has pyridine been employed for such stoichiometric oxidations, but also methyl substituted pyridines, 2,2'-bipyridine and quinuclidine. In fact, 2,2'-bipyridine has actually been observed to induce a much greater rate enhancement than pyridine for such stoichiometric oxidations. However, when such materials are employed with transition metal in an osmium catalytic oxidation, the rate of reaction is actually decreased, and in the case of 2,2'-bipyridine, the reaction is practically terminated. Thus, many of the conventional tertiary amine promoters in stoichiometric oxidations become inhibitors in the reaction system of the subject invention. Note also the close structural similarity between DABCO and quinuclidine and yet the drastic difference in performance as rate promoters.

The principles, preferred embodiments, and modes of

TABLE 1

| Run No. | Ex. or Comp. Ex. No. | Co. Cat. II Type | mmoles | pH of Product Sol. | Reaction Time (min.) | P.G. mmoles | Sel. (%) | Conv. (%) | P.G. Yield (%) |
|---|---|---|---|---|---|---|---|---|---|
| 1 | Comp. Ex. 1 | None | 0 | 3.5 | 20 | 16.0 | 75 | 3.0 | 2.23 |
| 2 | Ex. 1 | DABCO | 12.4 | 7.6 | 20 | 69.0 | 100 | 9.7 | 9.7 |
| 3 | Ex. 2 | HMTA | 12.4 | 5.2 | 20 | 36.0 | 100 | 5.04 | 5.04 |

DABCO = 1,4-diazabicyclo [2.2.2] octane
HMTA = hexamethylenetetramine
P.G. = propylene glycol

TABLE 2

| Run No. | Comp. Ex. No. | Co. Cat. II Type | mmoles | pH of product sol. | Reaction time (min.) | P.G. mmoles | Sel. (%) | Conv. (%) | P.G. Yield (%) |
|---|---|---|---|---|---|---|---|---|---|
| 4 | 2 | TEA | 12.4 | 7.5 | 20 | 9.4 | 100 | 1.3 | 1.3 |
| 5 | 3 | QNL | 12.4 | 8.6 | 20 | 9.7 | 100 | 1.4 | 1.4 |
| 6 | 4 | 2,2'-BIP | 12.4 | 5.5 | 20 | 0 | 0 | 0 | 0 |
| 7 | 5 | 1,4-DAB | 12.4 | 4.0 | 20 | 1 | 0 | 0 | 0 |
| 8 | 6 | BI | 12.4 | 5.0 | 20 | 6 | 70 | 1.2 | 0.8 |
| 9 | 7 | 1,3-DAB | 12.4 | 4.5 | 20 | 6 | 100 | 0.8 | 0.8 |
| 10 | 8 | TMED | 12.4 | 5.9 | 20 | 0 | 0 | 0 | 0 |
| 11 | 9 | Im | 12.4 | 5.2 | 20 | 15.5 | 100 | 2.2 | 2.2 |
| 12 | 10 | 1,8-DAN | 12.4 | 3.5 | 20 | 6.0 | 100 | 0.8 | 0.8 |
| 13 | 11 | 4,5-DAP | 12.4 | 5.5 | 20 | 0 | 0 | 0 | 0 |

TEA = Triethylamine
QNL = quinuclidine (1-azabicyclo[2.2.2]octane)
BIP = bipyridine
DAB = diazabenzene
BI = benzimidazoline (1H—1,3-diazaindene)
TMED = N,N,N',N'—tetramethylenediamine
Im = imidazole
DAN = diazanaphthalene
DAP = diazaphenanthrene

DISCUSSION OF RESULTS

Referring to Table 1, it can be seen that DABCO and HMTA can increase the rate of reaction by as much as 2 and 4 times (respectively) the rate in its absence.

Referring to Table 2, it can be seen that the mere possession of a tertiary nitrogen by a compound is not indicative of its ability to promote the subject reaction. Thus, triethylamine, (Run 4), N,N,N',N'-tetramethylenediamine (Run 10), 1-8-diazanaphthalene (Run operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for hydroxylating at least one olefinic compound having at least one ethylenic unsaturation which comprises reacting said olefinic compound in the presence of oxygen, water and a catalyst composition, in a manner and under conditions sufficient to convert catalytically at least one of said ethylenic unsaturation directly to its corresponding diol, said catalyst composition comprising:
   (a) at least one catalytically active osmium containing compound;
   (b) at least one transition metal containing Co-catalyst I having an identity and in an amount effective to increase at least one of the rate and selectivity of the hydroxylation reaction relative to its absence, said transition metal being copper; and
   (c) at least one Co-catalyst II selected from the group consisting of 1,4-diazabicyclo[2.2.2]octane and hexamethylenetetramine in an amount effective to increase the rate of the hydroxylation reaction relative to its absence.

2. The process of claim 1 wherein the osmium containing compound is selected from the group consisting of osmium oxide, osmium-halide, and mixtures thereof; Co-catalyst I comprises a transition metal copper salt having a cation and an anion, wherein said anion is of a member independently selected from the group consisting of halide, carboxylate, aryloate, aryolate, pseudo halide, $R_{10}S^-$, $HS^-$, $R_{10}Se^-$, $HTe^-$, $HSe^-$ and $R_{10}Te^-$, $R_{10}$ being alkyl of from about 1 to about 10 carbons.

3. The process of claim 1 wherein said catalyst composition additionally comprises at least one halo-source having an identity and in an amount effective to increase at least one of the rate and selectivity of the hydroxylation reaction relative to its absence.

4. The process of claim 3 wherein said halo-source is selected from the group consisting of halogenated organic hydrocarbon and halide salt wherein the cation of said salt is of a member independently selected from the group consisting of alkali metal, alkaline earth metal, tetrahydrocarbyl ammonium, and tetrahydrocarbyl phosphonium.

5. The process of claim 1 wherein the olefinic compound contains from about 2 to about 20 carbons.

6. The process of claim 1 wherein said Co-catalyst I is a copper halide salt.

7. The process of any one of claims 3, 4 and 5 wherein the identity and amount of the osmium in the osmium compound, Co-catalyst I, and halo-source, in said catalyst composition, are controlled to achieve in said composition a molar ratio of osmium:transition metal of Co-catalyst I:halogen in the halo-source of from about 1:1:1 to about 1:100:1000.

8. A process for directly hydroxylating olefins which comprises admixing to form a liquid reaction mixture comprising:
   (1) at least one olefinic compound having at least one ethylenic unsaturation;
   (2) at least one catalytically active osmium containing compound;
   (3) at least one transition metal containing Co-catalyst I having an identity and in an amount effective to increase at least one of the rate and selectivity of said hydroxylation reaction relative to its absence, wherein said transition metal is copper;
   (4) at least one Co-catalyst II selected from the group consisting of 1,4-diazabicyclo[2.2.2]octane and hexamethylenetetramine in an amount effective to increase at least one of the rate and selectivity of the hydroxylation reaction relative to its absence;
   (5) an oxygen containing gas; and
   (6) water in at least a stoichiometric molar ratio with the molar amount of ethylenic unsaturation to be hydroxylated in the olefinic compound; said admixing being conducted in a manner and under conditions sufficient to catalytically convert at least one of said ethylenic unsaturation directly to its corresponding diol.

9. The process of claim 8 wherein said liquid reaction mixture additionally comprises at least one inert organic solvent.

10. The process of claim 9 wherein said Co-catalyst II comprises less than about 15%, by weight, of said liquid reaction mixture, and said inert organic solvent comprises from about 10 to about 90%, by weight, of said liquid reaction mixture said inert organic solvent being dipolar and aprotic.

11. The process of claim 8 wherein said Co-catalyst I is a copper halide salt.

12. The process of claim 8 wherein said osmium compound is at least one osmium oxide.

13. The process of claim 12 wherein said osmium oxide is $OsO_4$.

14. The process of claim 8 wherein said osmium compound is at least one osmium-halide.

15. The process of claim 14 wherein said osmium-halide is represented by the structural formula $OsX_3$ wherein X is selected from the group consisting of Br, I, Cl, and mixtures thereof.

16. The process of claim 15 wherein X is selected from the group consisting of Br and Cl.

17. The process of claim 8 wherein said osmium compound is adsorbed on a support.

18. The process of claim 8 wherein said liquid reaction mixture further comprises a halo-source soluble in said liquid reaction mixture having an identity and in an amount effective to increase at least one of the rate and selectivity of the hydroxylation reaction relative to the absence of said halogen in said halo-source.

19. The process of claim 18 wherein said halo-source is selected from the group consisting of osmium-halide; copper halide; alkali metal halide; alkaline earth metal halide; tetrahydrocarbyl ammonium halide; tetrahydrocarbylphosphonium halide; halogenated hydrocarbon wherein the hydrocarbyl portion is selected from saturated aliphatic, saturated alicyclic, and aromatic; and mixtures thereof; and wherein in said liquid reaction mixture the mole ratio of osmium:copper:halogen of said halo-source present therein, is from about 1:10: to about 1:50:500.

20. The process of claim 18 wherein said halo-source is selected from the group consisting of copper halide; alkali metal halide; alkaline earth metal halide; tetrahydrocarbyl phosphonium halide; tetrahydrocarbyl ammonium halide; halogenated hydrocarbon wherein the hydrocarbyl portion thereof is selected from saturated aliphatic, saturated alicyclic and aromatic; and mixtures thereof; and wherein said liquid reaction mixture the mole ratio of osmium:copper:halogen present in said halo-source therein, is from about 1:15:20 to about 1:40:200.

21. The process of any one of claims 8 to 20 wherein said liquid reaction mixture is homogeneous, and wherein in said liquid reaction mixture the osmium compound is present in an amount sufficient to achieve a ratio of moles of osmium in the osmium compound to moles of ethylenic unsaturation to be hydroxylated of from about $1\times10^{-2}:1$ to about $1\times10^{-6}:1$; Co-catalyst I is present in an amount sufficient to achieve a ratio of moles of osmium in the osmium compound to moles of copper in Co-catalyst I of from about 1:500 to about 1:5; and Co-catalyst II is present in an amount sufficient to achieve a ratio of the moles thereof to the moles of copper in the Co-catalyst I of from about 1:1 to about 10:1; water is present in an amount sufficient to achieve a mole ratio of water to ethylenic unsaturation to be hydroxylated of from about 1:1 to about 10:1; and inert organic solvent, when present, is present in an amount of from about 20 to about 80%, by weight, based on the weight of said reaction mixture.

22. The process of claim 8 wherein said reaction mixture is substantially homogeneous and wherein in said reaction mixture: the osmium containing compound is selected from the group consisting of $OsO_4$, $OsBr_3$, $OsCl_3$, $Os_3(CO)_{12}$ and mixtures thereof; the Co-catalyst I is selected from the group consisting of $CuBr_2$, $CuCl_2$, and mixtures thereof, and Co-catalyst II comprises less than about 5%, by weight, of the reaction mixture.

23. The process of claim 22 wherein said olefin is selected from the group consisting of ethylene, propylene and mixtures thereof.

24. The process of claim 9 wherein the inert organic solvent comprises from about 20 to about 80%, by weight, of the reaction mixture and is selected from the group consisting of sulfolane, acetonitrile, N,N-dimethylacetamide, N,N-dimethylformamide, N-methylpyrrolidone, hydroxylated product and mixtures thereof.

25. The process of claim 24 wherein Co-catalyst I is $CuBr_2$; and the osmium compound is selected from the group consisting of $OsO_4$, $OsBr_3$ and mixtures thereof.

26. The process of claim 8 wherein the hydroxylation reaction temperature is from about 40° to about 250° C., and the reaction pressure is from about 300 to about 1500 psig.

27. The process of claim 8 wherein the Co-catalyst II is 1,4-diazabicyclo[2.2.2]octane.

28. The process of claim 8 wherein the Co-catalyst II is hexamethylenetetramine.

* * * * *